United States Patent
Xia et al.

(10) Patent No.: US 12,121,229 B2
(45) Date of Patent: Oct. 22, 2024

(54) SOFT-BODIED APPARATUS AND METHOD FOR OPENING EYELID

(71) Applicant: SHENZHEN INSTITUTES OF ADVANCED TECHNOLOGY CHINESE ACADEMY OF SCIENCES, Shenzhen (CN)

(72) Inventors: Zeyang Xia, Shenzhen (CN); Yangzhou Gan, Shenzhen (CN); Hao Deng, Shenzhen (CN); Jing Xiong, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 889 days.

(21) Appl. No.: 17/277,301

(22) PCT Filed: Feb. 5, 2021

(86) PCT No.: PCT/CN2021/075521
§ 371 (c)(1),
(2) Date: Mar. 18, 2021

(87) PCT Pub. No.: WO2022/165753
PCT Pub. Date: Aug. 11, 2022

(65) Prior Publication Data
US 2023/0100638 A1  Mar. 30, 2023

(51) Int. Cl.
*A61B 17/02* (2006.01)
*A61B 3/14* (2006.01)
(Continued)

(52) U.S. Cl.
CPC ............ *A61B 17/0231* (2013.01); *A61B 3/14* (2013.01); *A61B 34/32* (2016.02); *A61B 90/361* (2016.02);
(Continued)

(58) Field of Classification Search
CPC ... A61B 17/0231; A61B 34/32; A61B 90/361; A61B 2017/00057; A61B 2017/00212;
(Continued)

(56) References Cited

U.S. PATENT DOCUMENTS

| 4,604,787 A | * | 8/1986 | Silvers, Jr. | ............. | B23Q 7/046 |
| | | | | | 414/730 |
| 4,733,802 A | * | 3/1988 | Sheldon | ................ | A61F 9/0026 |
| | | | | | 604/302 |

(Continued)

FOREIGN PATENT DOCUMENTS

| CN | 107303240 A | 10/2017 |
| CN | 107753272 A | 3/2018 |

(Continued)

OTHER PUBLICATIONS

"A facial wearable robot for supporting eye opening and closure movement;" Kozaki et al., 2017 IEEE/RSJ International Conference on Intelligent Robots and Systems (IROS) (pp. 1812-1817), Sep. 1, 2017. (Year: 2017).*

(Continued)

*Primary Examiner* — Khoi H Tran
*Assistant Examiner* — Jorge O Peche
(74) *Attorney, Agent, or Firm* — Nitin Kaushik (57) ABSTRACT

A soft-bodied apparatus and a method for opening an eyelid are provided. The apparatus includes: a head support module, a real-time eyelid positioning module, a robot end-effector real-time positioning module, and an automatic eyelid opening operation module. The automatic eyelid (Continued)

opening operation module includes a robot body and a robot control system. The robot body is provided with a multi-axis rigid body mechanical arm and a soft-bodied end-effector. The robot control system takes the real-time poses of the upper and lower eyelids of the user as a motion target, and takes the real-time shape and the pose of the soft-bodied end-effector as feedback information to control motion of the robot body to automatically open the eyelid.

5 Claims, 4 Drawing Sheets

(51) Int. Cl.
| | |
|---|---|
| A61B 34/32 | (2016.01) |
| A61B 90/00 | (2016.01) |
| A61F 9/007 | (2006.01) |
| A61G 5/12 | (2006.01) |
| A61B 17/00 | (2006.01) |
| A61B 34/20 | (2016.01) |
| A61F 9/00 | (2006.01) |

(52) U.S. Cl.
CPC .............. *A61F 9/007* (2013.01); *A61G 5/121* (2016.11); *A61B 2017/00057* (2013.01); *A61B 2017/00592* (2013.01); *A61B 2034/2065* (2016.02); *A61B 2090/064* (2016.02); *A61B 2090/364* (2016.02); *A61B 2090/367* (2016.02); *A61F 2009/0035* (2013.01)

(58) Field of Classification Search
CPC ........ A61B 2090/064; A61B 2090/367; A61B 2034/2065; A61B 2090/371; A61B 34/30; A61F 9/007; A61F 2009/0035; A61F 2009/0052

See application file for complete search history.

(56) References Cited

U.S. PATENT DOCUMENTS

| | | | | | |
|---|---|---|---|---|---|
| 4,981,479 | A * | 1/1991 | Py | ................. | B05B 11/107 604/300 |
| 5,054,906 | A * | 10/1991 | Lyons, Jr. | ........... | A61B 17/0231 600/245 |
| 5,064,420 | A * | 11/1991 | Clarke | ................. | A61F 9/0026 604/301 |
| 5,133,702 | A * | 7/1992 | Py | ................. | A61F 9/0008 604/300 |
| 5,566,406 | A * | 10/1996 | Demeny | ................ | A61H 35/02 222/105 |
| 6,676,607 | B2 * | 1/2004 | de Juan, Jr. | ............ | A61B 34/76 600/452 |
| 7,320,692 | B1 * | 1/2008 | Bender | .............. | A61B 17/0644 623/23.72 |
| 8,942,828 | B1 * | 1/2015 | Schecter | .............. | A61H 31/007 607/116 |
| 9,489,753 | B1 * | 11/2016 | Bishop | ................. | G01B 21/20 |
| 9,775,512 | B1 * | 10/2017 | Tyler | ................. | G06V 40/19 |
| 9,821,475 | B1 * | 11/2017 | Lynn | ................. | F24S 23/74 |
| 10,817,722 | B1 * | 10/2020 | Raguin | ................. | G06V 40/40 |
| 11,266,511 | B1 * | 3/2022 | Hughes | ............. | A61B 17/1622 |
| 2002/0068992 | A1 * | 6/2002 | Hine | ................. | H01L 21/67259 700/229 |
| 2002/0163212 | A1 * | 11/2002 | Py | ................. | A45C 11/005 294/1.2 |
| 2002/0165790 | A1 * | 11/2002 | Bancroft | ............ | G06Q 30/0201 705/28 |
| 2003/0109885 | A1 * | 6/2003 | Tano | ................. | A61F 2/1662 606/107 |
| 2004/0005000 | A1 * | 1/2004 | Shake | .............. | H04B 10/07953 375/228 |
| 2005/0127693 | A1 * | 6/2005 | Py | ................. | A61F 9/0061 294/1.2 |
| 2005/0269113 | A1 * | 12/2005 | Plessala, Jr. | ........... | A01B 39/14 172/540 |
| 2006/0017297 | A1 * | 1/2006 | Py | ................. | A61F 9/0061 294/1.2 |
| 2006/0131904 | A1 * | 6/2006 | Mears | .................. | A61F 9/0061 294/1.2 |
| 2008/0081996 | A1 * | 4/2008 | Grenon | ................ | A61B 5/0066 600/443 |
| 2009/0161827 | A1 * | 6/2009 | Gertner | ................ | A61N 5/1017 378/65 |
| 2011/0092925 | A1 * | 4/2011 | Voss | .................. | A61B 5/1103 604/290 |
| 2012/0059517 | A1 * | 3/2012 | Nomura | ................ | B25J 15/0004 901/31 |
| 2012/0071840 | A1 * | 3/2012 | Bertelsen | ................ | A61H 35/02 604/302 |
| 2012/0190981 | A1 * | 7/2012 | Harris | ................. | A61B 5/14 604/95.01 |
| 2012/0253360 | A1 * | 10/2012 | White | ................. | A61B 34/35 606/130 |
| 2012/0296472 | A1 * | 11/2012 | Nagai | .................. | B25J 13/085 700/258 |
| 2012/0310184 | A1 * | 12/2012 | Pedersen | ................ | A61H 35/02 604/296 |
| 2013/0018281 | A1 * | 1/2013 | Nagale | ................. | A61B 5/1076 600/587 |
| 2013/0090640 | A1 * | 4/2013 | Nagale | ................ | A61B 18/1492 606/27 |
| 2013/0090648 | A1 * | 4/2013 | Nagale | ................. | A61B 5/202 606/1 |
| 2014/0018957 | A1 * | 1/2014 | Matsumoto | ............ | B25J 9/1692 700/251 |
| 2015/0032117 | A1 * | 1/2015 | Kim | .................. | A61B 17/3478 606/108 |
| 2015/0126970 | A1 * | 5/2015 | Thompson | ............ | A61F 9/0017 604/521 |
| 2015/0148597 | A1 * | 5/2015 | Ciulla | ................. | A61B 1/05 606/14 |
| 2015/0265467 | A1 * | 9/2015 | Hershoff | ................ | A61F 9/0061 606/107 |
| 2015/0335388 | A1 * | 11/2015 | Iida | ................. | A61B 34/30 606/130 |
| 2015/0366447 | A1 * | 12/2015 | Su | ................. | A61B 3/0016 351/206 |
| 2016/0193000 | A1 * | 7/2016 | Ogawa | ................... | A61B 34/74 606/130 |
| 2016/0214255 | A1 * | 7/2016 | Uhlenbrock | ........... | B25J 9/1674 |
| 2017/0024907 | A1 * | 1/2017 | Bermano | ................ | G06V 40/19 |
| 2017/0049320 | A1 * | 2/2017 | Nishizaki | ........... | A61B 17/0231 |
| 2017/0296430 | A1 * | 10/2017 | Barkholt | .............. | A61F 9/0026 |
| 2017/0348062 | A1 * | 12/2017 | Sweeney, II | ........... | A61B 34/32 |
| 2018/0049829 | A1 * | 2/2018 | Yates | .................... | A61B 34/30 |
| 2018/0050453 | A1 * | 2/2018 | Peters | .................... | B25J 19/021 |
| 2018/0071032 | A1 * | 3/2018 | de Almeida Barreto | ...................... G06T 19/006 |
| 2018/0116497 | A1 * | 5/2018 | Patterson | .................. | A61F 9/00 |
| 2018/0250822 | A1 * | 9/2018 | Shimodaira | ............ | B25J 9/1697 |
| 2018/0250823 | A1 * | 9/2018 | Shimodaira | ............ | B25J 9/1612 |
| 2019/0061163 | A1 * | 2/2019 | Yamaguchi | ............ | B25J 9/1664 |
| 2019/0142677 | A1 * | 5/2019 | Linder | .................... | A61F 7/034 601/18 |
| 2019/0357897 | A1 * | 11/2019 | Barash | .................. | A61F 9/0026 |
| 2019/0358083 | A1 * | 11/2019 | Barash | .................. | A61F 9/0026 |
| 2020/0000518 | A1 * | 1/2020 | Kiernan | ................ | A61B 5/6853 |
| 2020/0038101 | A1 * | 2/2020 | Tobey | ................. | A61B 18/1492 |
| 2020/0108506 | A1 * | 4/2020 | Goller | .................... | B25J 9/1697 |
| 2020/0155242 | A1 * | 5/2020 | Sweeney, II | ............ | A61B 34/71 |
| 2020/0189895 | A1 * | 6/2020 | Lessing | ..................... | B67C 3/24 |
| 2020/0261155 | A1 * | 8/2020 | Popovic | .................. | A61B 34/10 |
| 2020/0297358 | A1 * | 9/2020 | Cameron | ................ | A61B 90/11 |
| 2020/0345356 | A1 * | 11/2020 | Leimbach | ........ | A61B 17/07207 |
| 2020/0345357 | A1 * | 11/2020 | Leimbach | ........ | A61B 17/07207 |
| 2020/0345358 | A1 * | 11/2020 | Jenkins | ............ | A61B 17/07207 |
| 2020/0345359 | A1 * | 11/2020 | Baxter, III | ........ | A61B 17/07207 |
| 2020/0345360 | A1 * | 11/2020 | Leimbach | ................ | H04B 5/73 |

(56) References Cited

U.S. PATENT DOCUMENTS

| | | | |
|---|---|---|---|
| 2020/0345446 A1* | 11/2020 | Kimball | A61B 90/08 |
| 2020/0405375 A1* | 12/2020 | Shelton, IV | A61B 18/1815 |
| 2021/0015550 A1* | 1/2021 | Highsmith | A61B 18/1492 |
| 2021/0015551 A1* | 1/2021 | Fuentes-Ortega | A61B 18/1206 |
| 2021/0059745 A1* | 3/2021 | Highsmith | A61B 34/10 |
| 2021/0059777 A1* | 3/2021 | Overmyer | A61B 34/71 |
| 2021/0077183 A1* | 3/2021 | Basu | A61B 5/6853 |
| 2021/0077184 A1* | 3/2021 | Basu | A61B 34/20 |
| 2021/0085386 A1* | 3/2021 | Rao | A61B 5/287 |
| 2021/0121231 A1* | 4/2021 | Basu | A61B 18/1492 |
| 2021/0186458 A1* | 6/2021 | Giphart | A61B 17/0231 |
| 2021/0228281 A1* | 7/2021 | Calloway | A61B 34/20 |
| 2021/0244479 A1* | 8/2021 | Wassall | G02B 27/0172 |
| 2021/0276203 A1* | 9/2021 | Carithers | B25J 15/0441 |
| 2021/0339399 A1* | 11/2021 | Schluntz | G05D 1/0088 |
| 2021/0393353 A1* | 12/2021 | Campagna | A61B 90/14 |
| 2021/0401401 A1* | 12/2021 | Giphart | A61B 8/4281 |
| 2022/0133299 A1* | 5/2022 | Baxter, III | A61B 17/072 227/175.1 |
| 2022/0133300 A1* | 5/2022 | Leimbach | A61B 17/072 227/175.3 |
| 2022/0133301 A1* | 5/2022 | Leimbach | A61B 17/07207 227/175.1 |
| 2022/0133302 A1* | 5/2022 | Zerkle | A61B 17/072 227/175.4 |
| 2022/0133303 A1* | 5/2022 | Huang | A61B 17/072 227/175.1 |
| 2022/0133310 A1* | 5/2022 | Ross | A61B 17/072 227/176.1 |
| 2022/0133311 A1* | 5/2022 | Huang | A61B 90/06 227/176.1 |
| 2022/0133312 A1* | 5/2022 | Huang | A61B 17/072 227/176.1 |
| 2022/0133427 A1* | 5/2022 | Baxter, III | A61B 17/072 227/180.1 |
| 2022/0133428 A1* | 5/2022 | Leimbach | A61B 17/068 227/176.1 |
| 2022/0148333 A1* | 5/2022 | Funes Mora | G06T 1/60 |
| 2022/0227002 A1* | 7/2022 | Kouno | B25J 9/1697 |
| 2022/0233350 A1* | 7/2022 | Van Gorden | A61F 9/0026 |
| 2022/0257298 A1* | 8/2022 | Fox | A61B 18/00 |
| 2022/0346776 A1* | 11/2022 | Aronhalt | A61B 17/0644 |
| 2022/0346781 A1* | 11/2022 | Shelton, IV | A61B 17/0686 |
| 2022/0346784 A1* | 11/2022 | Shelton, IV | A61B 17/0686 |
| 2022/0362931 A1* | 11/2022 | Wheaton | B25J 9/1653 |
| 2022/0362944 A1* | 11/2022 | Zamani | B25J 19/021 |
| 2022/0378613 A1* | 12/2022 | Glozman | B25J 13/02 |
| 2022/0395275 A1* | 12/2022 | Diaz-Chiosa | A61B 17/0643 |
| 2023/0013731 A1* | 1/2023 | Nienaber | B25J 11/0075 |
| 2023/0083909 A1* | 3/2023 | Haro | H04N 7/157 345/619 |
| 2023/0100638 A1* | 3/2023 | Xia | A61B 34/30 600/202 |
| 2023/0146178 A1* | 5/2023 | Haro | G06F 3/04847 381/303 |
| 2023/0157872 A1* | 5/2023 | Glozman | A61B 34/71 606/167 |
| 2023/0165713 A1* | 6/2023 | Glozman | A61B 34/30 606/167 |
| 2023/0166411 A1* | 6/2023 | Harada | B25J 15/10 700/259 |
| 2023/0226685 A1* | 7/2023 | Gil | B25J 9/1628 700/253 |
| 2023/0233204 A1* | 7/2023 | Gil | A61B 34/25 606/1 |
| 2023/0255714 A1* | 8/2023 | Gil | B25J 9/1628 128/849 |
| 2024/0138905 A1* | 5/2024 | Okarski | A61B 18/1492 |
| 2024/0253246 A1* | 8/2024 | Smith | B25J 15/0095 |

FOREIGN PATENT DOCUMENTS

| | | | | |
|---|---|---|---|---|
| CN | 109843231 A | | 6/2019 | |
| CN | 111588469 A | * | 8/2020 | |
| CN | 112971877 A | * | 6/2021 | A61B 17/0231 |
| CN | 109431452 B | * | 8/2021 | A61B 3/10 |
| CN | 115533900 A | * | 12/2022 | |
| EP | 2080494 A1 | * | 7/2009 | A61B 17/0231 |
| EP | 4066749 A1 | * | 10/2022 | A61B 3/10 |
| JP | 2006277293 A | * | 10/2006 | |
| JP | 2009539509 A | * | 11/2009 | |
| JP | 2011200943 A | * | 10/2011 | B25J 13/085 |
| JP | 5391070 B2 | * | 1/2014 | G09G 5/06 |
| WO | WO-2012088471 A1 | * | 6/2012 | A61B 17/3403 |
| WO | WO-2020160097 A1 | * | 8/2020 | A61B 3/0033 |
| WO | WO-2020215121 A1 | * | 10/2020 | A61F 9/0061 |
| WO | WO-2020237939 A1 | * | 12/2020 | G06K 9/00201 |

OTHER PUBLICATIONS

"Kinect-Based Hand Tracking for First-Person-Perspective Robotic Arm Teleoperation," Bai et al., 2018 IEEE International Conference on Information and Automation (ICIA) (pp. 684-691), Aug. 1, 2018 (Year: 2018).*

"Chapter 2 Camera Calibration," Zhengyou Zhang, (https://www.semanticscholar.org/paper/Chapter-2-CAMERA-CALIBRATION-Zhengyou-Zhang-Zhang/6e20c43a0077d6580975625c44411e8c3fcf3ffe) Published 2009 (Year: 2009).*

* cited by examiner

SOFT-BODIED APPARATUS AND METHOD FOR OPENING EYELID

CROSS REFERENCE TO THE RELATED APPLICATIONS

This application is the national phase entry of International Application No. PCT/CN2021/075521, filed on Feb. 5, 2021, the entire contents of which are incorporated herein by reference.

TECHNICAL FIELD

The present disclosure relates to the field of medical instrument technology, and more particularly, to a soft-bodied apparatus and a method for opening an eyelid.

BACKGROUND

To prevent postoperative infection, eyes need to be cleaned and disinfected before ophthalmologic operation. In the process of eye cleaning before routine ophthalmologic operation, upper and lower eyelids need to be opened first to fully expose lacrimal passages, conjunctival sac and other parts for cleaning. At present, clinically medical staff mainly uses fingers to open the eyelids of patients to clean parts in the eyes.

In the existing technologies, there are some auxiliary instruments and equipment for eye cleaning. For example, the patent application CN201710253440.1 discloses an eye opening device for opening an upper eyelid and a lower eyelid. An operator can use this device to open the upper and lower eyelids of himself/herself or others. The patent application CN201780043837.6 discloses a device for cleaning an eye, which specifically includes a container and a locator. The patent application CN201711199743.6 discloses a comfortable ophthalmic eye washer. However, the existing auxiliary instruments and equipment for eye cleaning require the operator to directly open the upper and lower eyelids with the help of fingers or instruments, and there is no technical solution for automatically opening eyelids.

SUMMARY

An objective of the present disclosure is to overcome the above-mentioned defects of the existing technologies by providing a soft-bodied apparatus and a method for opening an eyelid, which can recognize and locate eyelids of patients in real time by using visual sensors, and then can automatically open the eyelids of the patients using robots based on the positioning information.

According to a first aspect of the present disclosure, there is provided a soft-bodied apparatus for opening an eyelid. The apparatus includes: a head support module, a real-time eyelid positioning module, a robot end-effector real-time positioning module, and an automatic eyelid opening operation module. The head support module is configured to support a head of a user. The real-time eyelid positioning module is configured to recognize and locate real-time poses of upper and lower eyelids of the user in real time. The robot end-effector real-time positioning module is configured to reconstruct a real-time shape and a pose of a robot soft-bodied end-effector. The automatic eyelid opening operation module includes a robot body and a robot control system. The robot body is provided with a multi-axis rigid body mechanical arm and a soft-bodied end-effector. The robot control system takes the real-time poses of the upper and lower eyelids of the user as a motion target, and takes the real-time shape and the pose of the soft-bodied end-effector as feedback information to control motion of the robot body to complete an action of automatically opening the eyelid of the user.

According to a second aspect of the present disclosure, there is provided a method for opening an eyelid using the above apparatus. This method includes:

recognizing and positioning real-time poses of upper and lower eyelids of the user in real time;

obtaining a real-time shape and a pose of the soft-bodied end-effector; and taking the real-time poses of the upper and lower eyelids of the user as a motion target, and taking the real-time shape and the pose of the soft-bodied end-effector as feedback information to control motion of the robot body to complete an action of automatically opening the eyelid of the user.

Compared with the existing technologies, the present disclosure has the advantage that as compared with manual operation, patients' eyelids can be opened quickly and accurately, burden of ophthalmologists and treatment costs can be effectively reduced, efficiency of ophthalmological treatment can be improved, and probability of cross infection can be reduced for both doctors and patients.

Other features and advantages of the present disclosure will become apparent from the following detailed description of exemplary embodiments of the present disclosure with reference to accompanying drawings.

BRIEF DESCRIPTION OF THE DRAWINGS

The accompanying drawings herein are incorporated in and constitute a part of this specification, illustrate embodiments of the present disclosure and, together with the specification, serve to explain the principles of the present disclosure.

DETAILED DESCRIPTION

Various exemplary embodiments of the present disclosure will now be described in detail with reference to the accompanying drawings. It is to be noted that the relative arrangement, numerical expressions, and numerical values of the components and steps set forth in these embodiments do not limit the scope of the present disclosure unless otherwise specifically stated.

The following description of at least one exemplary embodiment is actually merely illustrative, and in no way serves as any limitation on the present disclosure and application or use thereof.

Technologies, methods and equipment known to those of ordinary skill in the related art may not be discussed in detail, but where appropriate, the technologies, methods and equipment should be considered as part of the specification.

In all examples shown and discussed herein, any specific values should be interpreted as merely exemplary and not limiting. Therefore, other examples of the exemplary embodiment may have different values.

It is to be noted that similar reference numerals and letters indicate similar items in the following accompanying drawings. Therefore, once an item is defined in one drawing, there is no need to discuss this item further in subsequent drawings.

Figure 1:
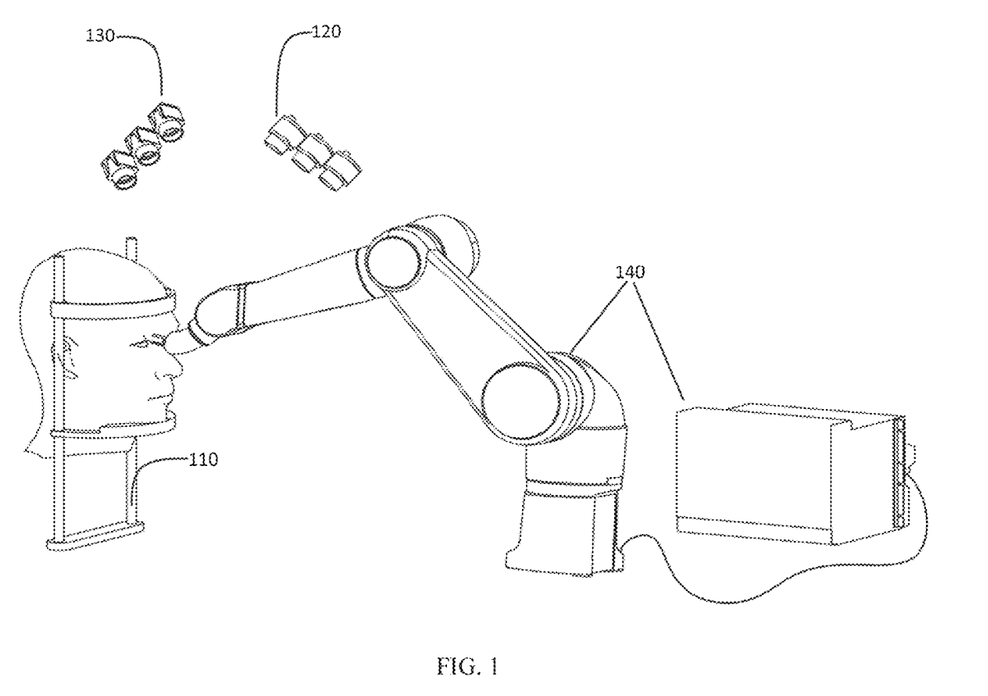
FIG. 1 is a schematic diagram showing an application scenario of a soft-bodied apparatus for opening an eyelid according to one embodiment of the present disclosure.

With reference to FIG. 1, a soft-bodied apparatus for opening an eyelid provided by the present disclosure includes a head support module 110 (also referred to as a head support component), a real-time eyelid positioning module 120, a robot end-effector real-time positioning module 130, and an automatic eyelid opening operation module 140.

The head support module 110 is configured to support a head of a patient to prevent the head of the patient from substantially moving during eye washing.

The real-time eyelid positioning module 120 is configured to recognize and position poses of upper and lower eyelids of the patient in real time using multiocular visual information.

The robot end-effector real-time positioning module 130 is configured to reconstruct a shape and a pose of a soft-bodied robot end-effector in real time using the multiocular visual information.

The automatic eyelid opening operation module 140 includes a robot body and a robot control system. The robot body includes a multi-axis rigid body mechanical arm and a soft-bodied end-effector. The robot control system takes the real-time pose of the eyelid of the patient as a motion target, and takes the real-time shape and pose information of the soft-bodied end-effector as feedback information to control motion of the robot body to complete the action of automatically opening the eyelid of the patient.

Figure 2:
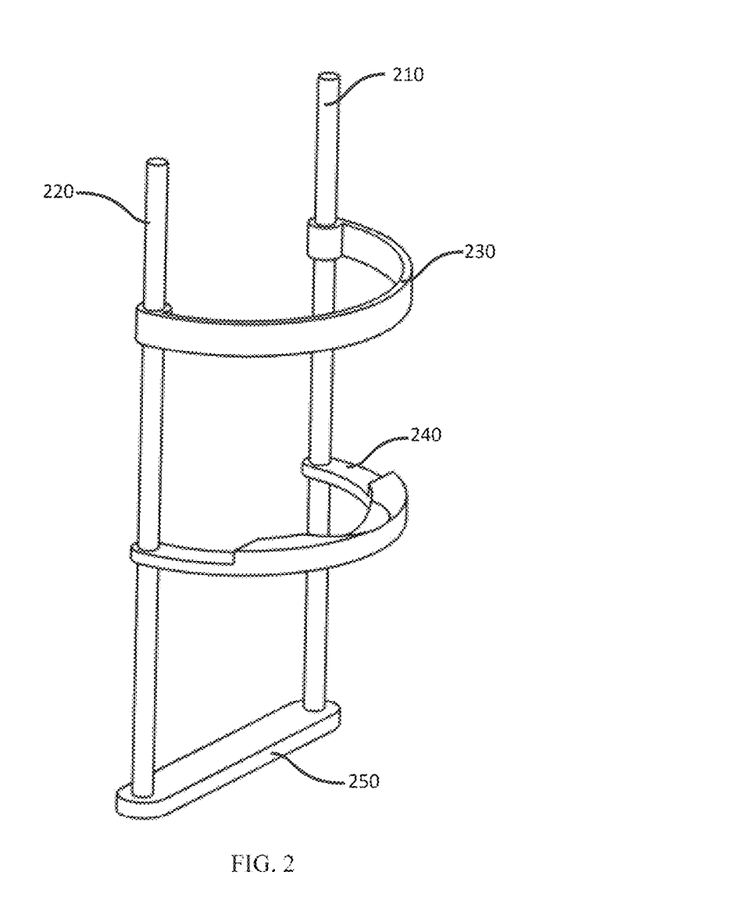
FIG. 2 is a schematic structural diagram of a head support module according to one embodiment of the present disclosure.

Specifically, the head support module supports and fixes the head of the patient through an underjaw support plate and a forehead rest, to prevent the head of the patient from substantially moving during eye washing. As shown in FIG. 2, the head support module includes two side support members 210 and 220, the underjaw support plate 240, the forehead rest 230, and a base 250. Two ends of the underjaw support plate 240 are attached to the two side support members 210 and 220 respectively, and the underjaw support plate 240 is configured to surround the neck of the user to provide support for the underjaw of the user. The forehead rest 230 is also attached to the two side support members 210 and 220 and is configured to surround the head of the patient to fix the head. The base 250 is combined with the two side support members 210 and 220 to form an integrated framework of the head support module.

It is to be noted that the head support module may have various different shapes of integrated frameworks. For example, shapes of the head support module include roughly square, rectangle, trapezoid, etc., or other regular or irregular polygonal shapes.

Figure 3:
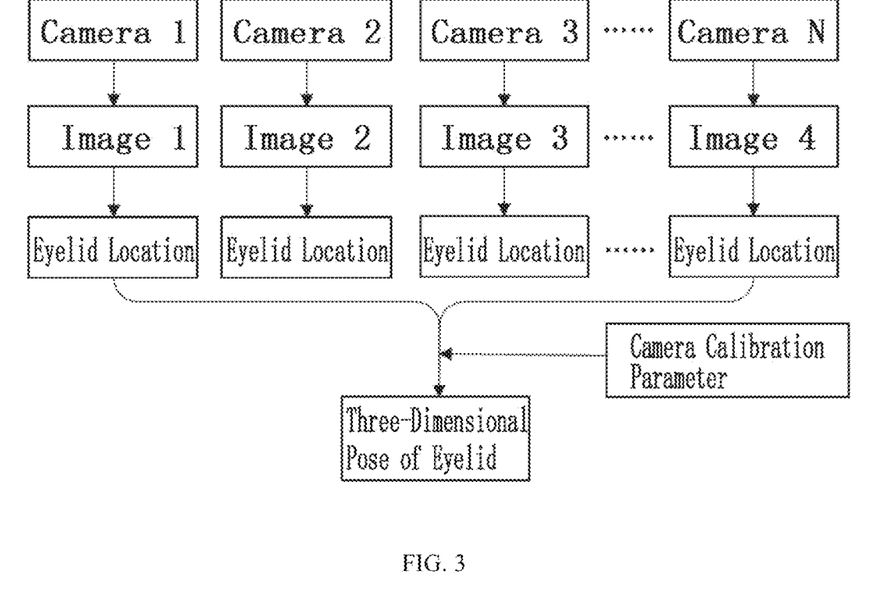
FIG. 3 is a schematic diagram showing an overall process of eyelid positioning according to one embodiment of the present disclosure.

The real-time eyelid positioning module 120 uses a visual detection method to detect the pose of the eyelid in real time, and an overall solution is as shown in FIG. 3. A camera is inevitably blocked in the process of eye cleaning. Preferably, based on multiocular vision principles, a plurality of cameras are arranged to photograph images of the eyelid from different angles. For the images obtained by each of the cameras, a target detection algorithm (such as YOLO v3, etc.) is employed to extract a location of an eye of the patient, and then the pose of the eyelid is obtained by calculating according to a relative location between the eye and the eyelid and the shape of the eyelid, etc. For example, after the location of the same eyelid is obtained from the images photographed by more than two cameras, a three-dimensional pose of a target eyelid is obtained by calculating by using a principle of multiocular stereo vision in combination with a camera calibration parameter, wherein the three-dimensional pose is configured for indicating the location and the direction of the eyelid. The camera calibration parameter includes an intrinsic parameter of each camera and extrinsic parameters of different cameras, and the camera calibration parameter may be obtained by using methods such as a Zhang Zhengyou's calibration method. In the above process, each of the cameras synchronously and dynamically collects images, to implement the real-time positioning of the eyelid.

Figure 4:
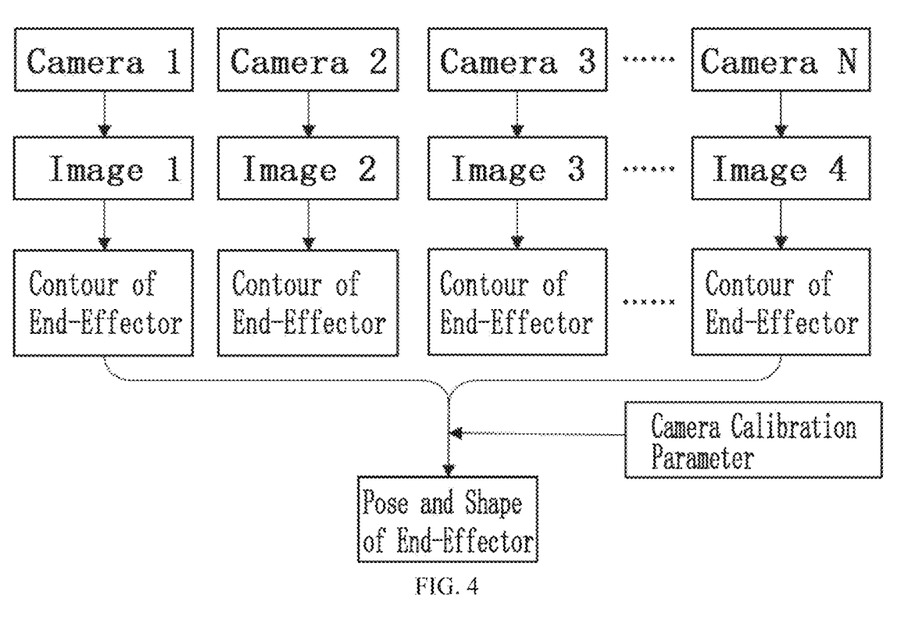
FIG. 4 is a schematic diagram showing an overall process of soft-bodied end-effector positioning according to one embodiment of the present disclosure.

The robot end-effector real-time positioning module 130 is configured to position a soft-bodied robot end-effector in real time to ensure accuracy and safety of the operation of the soft-bodied robot in the process of automatically opening the eyelid. As shown in FIG. 4, a multiocular vision solution similar to the eyelid positioning method is still used. A contour of the soft-bodied robot end-effector is extracted for an image obtained by each of the cameras by using, for example, a threshold segmentation method based on color features. Next, a pose and a three-dimensional shape of the soft-bodied robot end-effector may be obtained by using a principle of multiocular stereo vision in combination with a camera calibration parameter, to implement the positioning of the end-effector. The camera calibration parameter includes an intrinsic parameter of each camera and extrinsic parameters of different cameras, and the camera calibration parameter may be obtained by using methods such as a Zhang Zhengyou's calibration method. In the above process, each of the cameras synchronously and dynamically collects images, to implement the real-time positioning of the soft-bodied end-effector.

In one embodiment, to extract the contour of the robot end-effector, a marker with obvious color or shape features may be pasted onto the end-effector, such that the contour of the end-effector may be determined by extracting features of the marker.

The automatic eyelid opening operation module 140 includes a robot body and a robot control system. The robot body is composed of a multi-axis rigid body mechanical arm and a soft-bodied end-effector arranged at an end of the multi-axis rigid body mechanical arm. The multi-axis rigid body mechanical arm may be fixedly mounted on a treatment couch, a treatment chair or a movable platform. The soft-bodied end-effector is prepared from a flexible soft-bodied deformable material fitting to an eyelid structure, and is controlled by, for example, pneumatic drive to move. Further, a flexible force sensor is integrated on the soft-bodied end-effector to feed back force information of the soft-bodied end-effector in real time.

In the embodiments of the present disclosure, by controlling the motion of the multi-axis rigid body mechanical arm, the robot body can be ensured to move to the location of the target eyelid as quickly as possible. Accuracy of eyelid opening and comfort of the patient can be ensured by arranging the soft-bodied end-effector at the end of the mechanical arm and combining with the pneumatic drive. Furthermore, by means of the flexible force sensor arranged on the soft-bodied end-effector and in combination with feedback of the force information, the robot control system can timely and accurately adjust the force and the angle of the operation on the eyelid, to provide maximum comfort for the patient and ensure operation safety under the premise of quickly completing the operation of eyelid opening.

In one embodiment, the end-effector is configured to be fit for simulating the operation of opening the eyelid with a finger. For example, the end-effector is provided with a flexible finger-like protrusion and a tooth-like protrusion, and the eyelid is opened by controlling the engagement time, the turning angle, and the turning force of the finger-like protrusion and the tooth-like protrusion. The turning angle and the turning speed in this method are easy to accurately control, such that a probability of damaging an eyeball is reduced, work efficiency is improved, and pain of the patient is decreased. For another example, the end-effector is provided with an arc-shaped eyelid opener connected to a rotating shaft. By controlling rotation of the rotating shaft, the eyelid opener is driven to perform the operation of eyelid opening.

Figure 5:
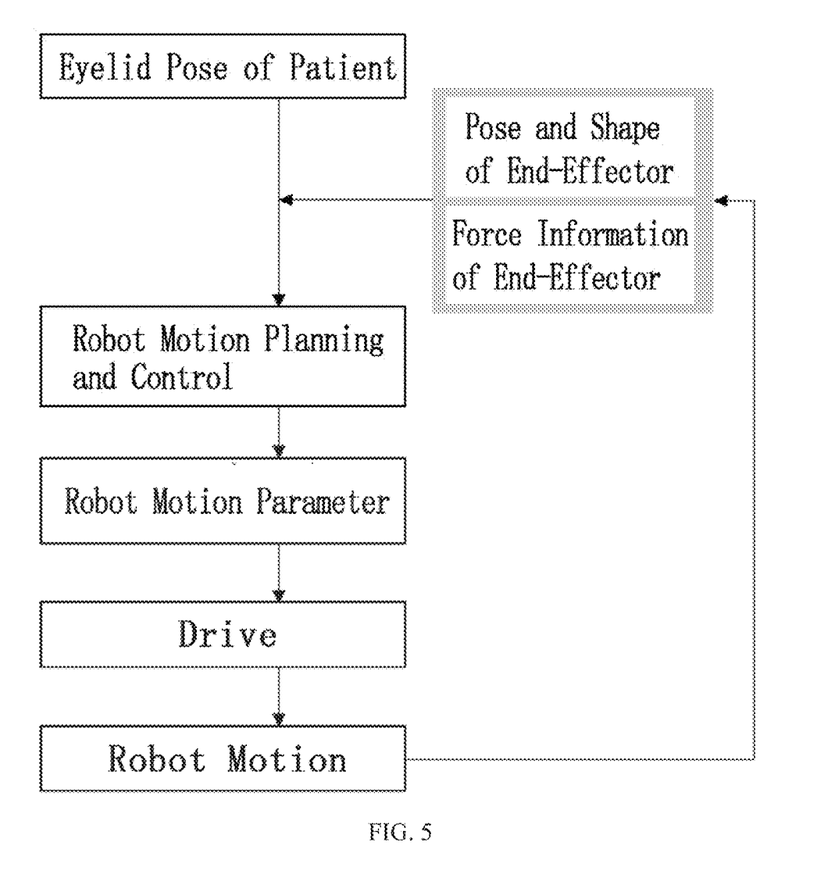
FIG. 5 is an overall flow diagram of implementing an eyelid opening operation using a robot control system according to one embodiment of the present disclosure.

FIG. 5 is an overall flow diagram of completing an eyelid opening operation by controlling the robot body by the robot control system. Specifically, the control system takes the patient's eyelid real-time pose extracted by the real-time eyelid positioning module as an operation target, takes the pose and the shape of the soft-bodied end-effector and force information of the soft-bodied end-effector as feedback signals, and obtains motion parameters of the robot based on motion planning and control algorithms. These motion parameters are configured for limiting the motion of the robot body. Finally, a drive in the control system takes the motion parameters of the robot as input, and drives the robot to move by controlling underlying mechanisms such as a motor and a pneumatic valve in the robot body.

It is to be understood that to control the robot for completing the task of eyelid opening as required, it is required to determine a relative positional relationship between the robot and external environment, especially the location and the pose of the robot end-effector. If a configuration of one robot has been determined, geometric information and joint information of constituent parts of this robot are known. Therefore, a desired operation may be achieved by controlling the robot after obtaining the pose of the robot end-effector with respect to a reference coordinate system. A specific process of driving the robot to move is omitted herein.

It is to be noted that those skilled in the art may make appropriate changes and modifications to the above-mentioned embodiments without departing from the spirit and scope of the present disclosure. For example, visual sensors used in the real-time eyelid positioning module and the robot end-effector real-time positioning module may be depth cameras or RGB-D cameras (color-depth cameras), etc. The extraction of the real-time location of the eyelid, the extraction of the contour of the end-effector, and calibration of a multiocular camera may also be implemented by using other image processing algorithms.

The robot control system in the present disclosure may be a system, a method, and/or a computer program product. The computer program product may include a computer readable storage medium having computer readable program instructions thereon for causing a processor to carry out aspects of the present disclosure.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. More specific examples (a non-exhaustive list) of the computer readable storage medium include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. The computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical fiber transmission, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++, Python or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In a scenario involved with the remote computer, the remote computer may be coupled to the user's computer through any type of network, including a local area network (LAN) or a wide area network (WAN), or may be coupled to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described with reference to flowcharts and/or block diagrams according to the method, apparatus (system) and a computer program product of the embodiments of the present disclosure. It is to be understood that each block of the flowcharts and/or block diagrams, and combinations of blocks in the flowcharts and/or block diagrams, can be implemented by the computer readable program instructions.

These computer readable program instructions may be provided to a processor of a general purpose computer, special purpose computer, or other programmable data processing apparatus to produce a machine, such that these instructions, which execute via the processor of the computer or other programmable data processing apparatus, create means for implementing the functions/acts specified in one or more blocks in the flowcharts and/or block diagrams. These computer readable program instructions may also be stored in a computer readable storage medium that can direct a computer, a programmable data processing apparatus, and/or other devices to function in a particular manner, such that the computer readable medium having instructions stored therein includes an article of manufacture including instructions which implement aspects of the function/act specified in one or more blocks in the flowcharts and/or block diagrams.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in one or more blocks in the flowcharts and/or block diagrams.

The flowcharts and block diagrams in the accompanying drawings illustrate architectures, functions and operations of possible implementations of systems, methods, and computer program products according to a plurality of embodiments of the present disclosure. In this regard, each block in the flowcharts or block diagrams may represent a module, a program segment, or a portion of instructions, which includes one or more executable instructions for implementing the specified logical function(s). In some alternative implementations, the functions denoted by the blocks may occur in a sequence different from the sequences shown in the accompanying drawings. For example, two blocks shown in succession may, in fact, be executed substantially concurrently, or the blocks may sometimes be executed in a reverse sequence, depending upon the functions involved. It is also to be noted that each block in the block diagrams and/or flowcharts and/or a combination of the blocks in the block diagrams and/or flowcharts may be implemented by a special-purpose hardware-based system executing specific functions or acts, or by a combination of a special-purpose hardware and computer instructions. It is well known to those skilled in the art that implementations by means of hardware, implementations by means of software and implementations by means of software in combination with hardware are equivalent.

The descriptions of the various embodiments of the present disclosure have been presented above for purposes of illustration, but are not intended to be exhaustive or limited to the embodiments disclosed. Therefore, it is apparent to an ordinary skilled person in the art that modifications and variations could be made without departing from the scope and spirit of the embodiments. The terminology used herein is chosen to best explain the principles of the embodiments, the practical application or technical improvement over technologies found in the marketplace, or to enable others of ordinary skill in the art to understand the embodiments disclosed herein. The scope of the present disclosure is limited by the appended claims.

What is claimed is:

1. A soft-bodied apparatus for opening an eyelid, comprising: a head support module, a real-time eyelid positioning module, a robot end-effector real-time positioning module, and an automatic eyelid opening operation module, wherein: the head support module is configured to support a head of a user; the real-time eyelid positioning module is configured to recognize and locate real-time poses of upper and lower eyelids of the user in real time; the robot end-effector real-time positioning module is configured to reconstruct a real-time shape and a pose of a soft-bodied end-effector of a robot; the automatic eyelid opening operation module comprises a robot body and a robot control system; wherein the robot body is provided with a multi-axis rigid body mechanical arm and the soft-bodied end-effector, and the robot control system takes the real-time poses of the upper and lower eyelids of the user as a motion target, and the robot control system takes the real-time shape and the pose of the soft-bodied end-effector as feedback information to control a motion of the robot body to complete an action of automatically opening the eyelid of the user;

wherein the soft-bodied end-effector is prepared from a flexible soft-bodied deformable material fitting to an eyelid structure and is arranged at an end of the multi-axis rigid body mechanical arm, and the soft-bodied end-effector is controlled by pneumatic drive to implement an eyelid opening action;

wherein the robot end-effector real-time positioning module is configured to:

obtain soft-bodied end-effector images photographed by a plurality of cameras from different angles;

segment a contour of the soft-bodied end-effector for an image obtained by each of the plurality of cameras by using the contour of the soft-bodied end-effector and a distinction threshold of a color feature of a surrounding area; and obtain, for the contour of the soft-bodied end-effector obtained by the plurality of cameras, a pose and a three-dimensional shape of the soft-bodied end-effector by using a principle of multiocular stereo vision in combination with a camera calibration parameter, to implement positioning of the soft-bodied end-effector;

wherein a flexible force sensor is integrated on the soft-bodied end-effector to feed back, in real time, force information of the soft-bodied end-effector to the robot control system, and the robot control system adjusts an operating force of the soft-bodied end-effector according to the force information;

wherein the soft-bodied end-effector is provided with a marker, and the contour of the soft-bodied end-effector is determined by extracting a feature of the marker.

2. The soft-bodied apparatus for opening the eyelid according to claim 1, wherein the head support module comprises two side support members, an underjaw support plate, a forehead rest, and a base; wherein the underjaw support plate is attached to the two side support members and is configured to surround a neck to provide support for an underjaw, the forehead rest is attached to the two side support members and is configured to securely surround the head to maintain the head in a desired pose, and the base is combined with the two side support members to form an integrated framework for supporting the head.

3. The soft-bodied apparatus for opening the eyelid according to claim 1, wherein the real-time eyelid positioning module is configured to:
- obtain the user's eye images photographed by a plurality of cameras from different angles to extract location information of a corresponding eye respectively;
- calculate to obtain location information of the eyelid by using a relative location between the corresponding eye and the eyelid and a shape of the eyelid; and
- calculate to obtain, for the location information of the eyelid obtained by the plurality of cameras, a three-dimensional pose of a target eyelid by using a principle of multiocular stereo vision in combination with a camera calibration parameter, wherein the three-dimensional pose is configured for limiting a location and a direction of the eyelid.

4. The soft-bodied apparatus for opening the eyelid according to claim 3, wherein the camera calibration parameter comprises an intrinsic parameter of each camera of the plurality of cameras and extrinsic parameters of the plurality of cameras.

5. The soft-bodied apparatus for opening the eyelid according to claim 1, wherein the multi-axis rigid body mechanical arm is configured to be fixedly mounted on a treatment couch, a treatment chair or a movable platform.

* * * * *